United States Patent [19]

Tkatchenko et al.

[11] Patent Number: 4,709,087

[45] Date of Patent: Nov. 24, 1987

[54] PROCESS FOR THE SYNTHESIS OF ISOCYANATES AND OF ISOCYANATE DERIVATIVES

[75] Inventors: Igor Tkatchenko, Caluire; Rabih Jaouhari, Rennes; Michel Bonnet, Toulouse; Gordon Dawkins, Kirkliston; Serge Lecolier, Janville sur Juine, all of France

[73] Assignee: Societe Nationale des Poudres et Explosifs, Paris, France

[21] Appl. No.: 813,947

[22] Filed: Dec. 27, 1985

[30] Foreign Application Priority Data

Dec. 28, 1984 [FR] France ................................ 84 19969

[51] Int. Cl.⁴ .............................................. C07C 71/00
[52] U.S. Cl. ................................................... 560/339
[58] Field of Search ........................................... 560/339

[56] References Cited

U.S. PATENT DOCUMENTS

| | | | |
|---|---|---|---|
| 3,201,433 | 8/1965 | Manes | 560/339 |
| 3,558,684 | 1/1971 | Von Brachel et al. | |
| 3,914,311 | 10/1976 | Coulson | |
| 3,948,966 | 4/1976 | Inamoto | 560/339 |
| 4,130,577 | 12/1978 | Wako et al. | |
| 4,399,074 | 8/1983 | Schaefer | 560/339 |

FOREIGN PATENT DOCUMENTS 0088218 9/1983 European Pat. Off. .

OTHER PUBLICATIONS

Structure and Mechanism in Organic Chemistry (Second Edition), by C. K. Ingold, Cornell Univ. Press, 1969, pp. 558-561.

"Recent Advances in Isocyanate Chemistry," Shoichiro Ozaki, *Chemical Reviews*, vol. 72, No. 5, Oct. 1972, pub. by American Chemical Soc., pp. 457-496.

*Inorganic Synthesis*, vol. XVII, 1977, McGraw-Hill Book Co., Alan G. MacDiarmid, Ed-in-Chief, pp. 120-122.

"The in Situ-generated Nickel(0)-catalyzed Reaction of Aryl Halides with Potassium Iodide and Zinc Powder," Kentaro Takagi et al, 1980, Bulletin Chemical Society of Japan 53-3691-3695, Dec. 1980.

*Primary Examiner*—Alan M. Siegel
*Attorney, Agent, or Firm*—Burns, Doane, Swecker & Mathis

[57] ABSTRACT

The present invention relates to a process for the synthesis of isocyanates and of isocyanate derivatives. Isocyanates are obtained by reacting an organic halide with a metal cyanate in an organic medium in the presence of a catalyst consisting of a complex of nickel with at least one organic ligand, in which complex the nickel is in the zero oxidation state.

A carbamate or a urea, respectively, are obtained by a subsequent reaction with a hydroxy compound or a primary or secondary amine.

Isocyanates and their derivatives are used especially either as refined synthesis agents for the production of pesticides and medications, or as monomers or comonomers for the preparation of many macromolecular compounds.

14 Claims, No Drawings

PROCESS FOR THE SYNTHESIS OF ISOCYANATES AND OF ISOCYANATE DERIVATIVES

The invention relates to a new process for the synthesis of isocyanates and of isocyanate derivatives from organic halides and metal cyanates, according to the general reaction sequence:

$$RX + NCOM \longrightarrow MX + RNCO \xrightarrow{ZH} RNHCOZ \quad (1)$$

in which R denotes an organic group, X a halogen, M a metal and ZH an organic compound containing labile hydrogen, for example an alcohol or a primary or secondary amine.

The isocyanate derivatives of special concern are carbamates and ureas. These derivatives and the isocyanates are used especially either as fine synthesis agents for the production of pesticides and medications, or as monomers or comonomers in the preparation of many macromolecular compounds, such as polyurethanes, which have a very wide variety of applications.

The synthesis of isocyanates and of isocyanate derivatives according to the reaction sequence (1) is known.

S. Ozaki (Chem. Rev. 1972, 72, 457) and, more recently, articles by K. Findeisen, K. König and R. Sunderman (Houben-Weyl, Methoden der Organischen Chemie Vol E 4, 1984, pp. 738-784) and by J. Ippen (ibid., pp. 784-802) give a summary of the fields of application of the reaction sequence (1). In particular, the reaction takes place under relatively mild conditions when alkyl halides are employed, bromides being more reactive than chlorides. Benzyl and allyl halides are also reactive. On the other hand, these articles do not describe the synthesis of aryl isocyanates and of vinyl isocyanates according to this method.

A number of patents describe various improvements introduced into the synthesis of carbamates, alkyl isocyanates, allyl isocyanates and benzyl isocyanates. The most widely deScribed improvement ponsists in dissolving the cyanate ion in an organic medium, usually a dipolar aprotic medium.

To this end, Japanese patent application 75/84,528 describes the use of crown ethers and of tetraalkylammonium cyanates, and EP 88,218 describes bis(pyridine)zinc cyanate which is produced by the reaction of alkali metal cyanates, zinc chloride and pyridine.

U.S. Pat. No. 3,558,684 describes the preparation of alkenyl isocyanates by the reaction of an alkenyl halide with an alkali metal cyanate in the presence of a catalyst consisting of metallic copper and of a cuprous halide.

U.S. Pat. No. 4,130,577 describes the preparation of benzyl isocyanates by the reaction of a benzyl halide with an alkali metal cyanate in the presence of a catalyst consisting of a metal (V, Mn, Co, Zn, Pd and Sn) and of salts of these metals.

FR Pat. No. 2,464,249 describes a process for the synthesis of methyl isocyanate by the reaction of $CH_3Cl$ with NCOK in the presence of KI or of KBr.

Japanese patent applications No. 75/84,528 and 75/84,529 specifically mention the preparation of phenyl isocyanate by the reaction of chlorobenzene with potassium cyanate under phase-transfer conditions.

The synthesis of heterocyclic or aromatic or vinyl isocyanates by the reaction of a halogenated heterocyclic compound or of a halogenated aromatic or vinyl compound with a metal cyanate in a solely organic medium has not been described, so far as the Applicant Company is aware.

It is well known that the reactivity of carbonhalogen $sp^2$ bonds, such as are found in vinyl and aryl halides, towards nucleophilic agents is much lower than that of carbon-halogen $sp^3$ bonds (C. K. Ingold, "Structure and Mechanisms in Organic Chemistry", 2nd ed., Cornell University Press, Ithaca, 1969, p. 559). A particular objective of the present invention is to overcome this lack of reactivity.

According to the invention, the process for the synthesis of isocyanates and of isocyanate derivatives is characterized in that the reaction between the organic halide and the metal cyanate, in an organic medium, takes place in the presence of a catalyst consisting of a complex of nickel with at least one organic ligand, in which complex the nickel is in the zero oxidation state.

The isocyanate derivatives which are of particular concern have the general formula RNHCOZ, in which R denotes an organic group and Z a group chosen from the class consisting of alkoxy and amino (un-, mono- or di-substituted $NH_2$) groups. They are obtained by reacting the isocyanate formed by the reaction between the organic halide and the metal cyanate with a compound of formula ZH, Z having the abovementioned meaning.

When ZH is a hydroxy compound, a carbamate is obtained and, when ZH is a primary or secondary amine, a urea is obtained.

To give illustrative examples without implying any limitation, ZH can be ethanol, methanol, isopropanol, tertbutanol, 2-ethylhexanol, cyclohexanol, ethylene glycol, a phenol, a cresol, a naphthol, dimethylamine, diethylamine, butylamine or aniline.

The compound of formula ZH is preferably added in a single portion to the reaction medium at the beginning of the reaction between the organic halide and the metal cyanate.

According to another, particularly preferred, alternative embodiment, the compound of formula ZH is added to the reaction medium as at least one portion during the reaction between the organic halide and the metal cyanate. The compound ZH may be added, for example, in two portions, at the beginning of a reaction and then at two-thirds of the overall reaction period.

The molar ratio of the ZH compound to the starting organic halide may be any whatever but is preferably in the region of 1. In a particularly preferred manner, this ratio is slightly greater than 1.

As a result, the process according to the invention makes it possible to obtain, simply and economically, many isocyanates and their derivatives containing various functional groups which are insensitive to the reaction conditions, without involving the use of phosgene, a particularly toxic compound, including (a fact whose importance must be well appreciated) heterocyclic or aromatic or vinyl isocyanates and their derivatives.

The organic halide is preferably chosen from the group consisting of:

Acyclic or cyclic vinyl halides, optionally substituted by at least one alkyl or aryl group. Examples which can be mentioned are vinyl bromide, 1-bromo-1propene, and 1-bromo-2-phenylethylene.

Simple or condensed aromatic halides, optionally substituted by at least one alkyl, vinyl, aryl, halo or alkoxy group. The examples which can be mentioned are chloro-, bromo- or iodobenzene, para-bromoanisole, parabromotoluene, para-bromochlorobenzene, para-bromofluorobenzene and chloro- or bromonaphthalenes, Halogenated heterocyclic compounds such as bromopyridines and 3-bromofuran, Allyl halides, optionally substituted by at least one alkyl or aryl group, such as allyl bromide, 2-methallyl chloride and cinnamyl bromide, Straight-chain or cyclic or branched aliphatic halides such as chloro-, bromo- or iodomethane, 1-chlorobutane, 1,4-dichlorobutane and bromocyclohexane, and benzyl halides, optionally substituted by at least one alkyl or aryl group, such as benzyl chloride or bromide and cumyl chloride or bromide.

In a particularly preferred manner, the organic halide is chosen from the group consisting of the abovementioned vinyl halides and the abovementioned aromatic halides.

As a general rule, better yields are obtained with iodides and bromides than with chlorides. The reactivity order which is observed is:

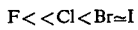

A particular characteristic of the invention is that the reactivity of the chlorides, and consequently the reaction yield, can be increased by adding an alkali metal or onium bromide or chloride to the reaction medium, this being equivalent to a chlorine/bromine (or iodine) exchange in the organic chloride. The addition of a molar fraction of the order of 10% is generally sufficient to produce a substantial increase in the conversion of the organic chloride.

The metal cyanate employed is preferably an alkali metal or alkaline-earth metal cyanate. Sodium or potassium cyanates, being commercially available, are of obvious practical interest. More particularly, sodium cyanate, which is more soluble than potassium cyanate, will be employed. All metal cyanates are obviously suitable and enable the invention to be implemented.

The molar ratio NCOM/RX can have any value but is preferably chosen slightly higher than 1; a ratio between 1.15 and 1.35 is especially preferred.

The process according to the invention is characterized in that the reaction between the organic halide and the metal cyanate takes place in the presence of a catalyst consisting of a complex of nickel with at least one organic ligand.

The organic ligand(s) preferably contains (contain) phosphorus, but arsenic-containing ligands, for example, and ligands consisting solely of hydrocarbons, such as cyclo-octadiene or cyclododecatriene ligands are also suitable.

When the ligand(s) contains (contain) phosphorus, it (or they) can be monodentate or multidentate. Basic phosphines and bidentate phosphines are particularly preferred. Bidentate phosphines are understood to mean the phosphorus compounds of general structure $R_1R_2P$—$(CH_2)_n$—$PR_3R_4$ in which the substituents $R_1$, $R_2$, $R_3$ and $R_4$ are alkyl or aryl groups. Among basic phosphines, tributyl-, trihexyl-and trioctylphosphines, tricyclohexylphosphine, dimethylphenylphosphine and methyldiphenylphosphine can be mentioned in particular.

The complexes $Ni(PPh_3)_4$, $Ni(PPh_3)_3$, $Ni(PBu_3)_4$ and $Ni(PCy_3)_2$, where Ph denotes phenyl, Bu butyl and Cy cyclohexyl, are preferred.

Among the bidentate phosphines, there can be mentioned bis(diphenylphosphino)polymethylene and especially bis(diphenylphosphino)ethane and -butane (abbreviated to dppe and dppb, respectively), which are preferred. The activity of the complexes is found to follow the order Ni [$PH_2P$ $(CH_2)_n PPh_2]_2$ n=1<2>-3<4

In this case, the nickel/phosphorus ratio corresponds to that of the preformed complexes, namely 1/4, but it will be preferably chosen equal to 1/2 as, for example, in the complexes $Ni(Ph2P(CH_2)_nPPh_2)$ which are formed in situ.

The preparation of such phosphorus complexes can be carried out according to the method described in Inorg. Synth. 1977, 17, 121, but is preferably advantageously carried out in situ by the addition of one equivalent of diphosphine or of 2 equivalents of monophosphine to zero-valent nickel complexes such as bis(cyclooctadiene)nickel (abbreviated to Ni(cod)$_2$) or (1,5,9-cyclododecatriene)nickel, which are themselves prepared according to the method described in Inorg. Synth. 1974, 15, 5.

It is also possible to prepare and use a zero-valent nickel complex containing a basic phosphine ligand and a bidentate phosphine ligand, such as the complex Ni(dppe)(PPh$_3$)$_2$.

When the ligand(s) contains (contain) arsenic, a tertiary arsine such as, for example, triphenylarsine, will be preferred.

As an example, the catalysts Ni(AsPh$_3$)$_4$ and Ni-(AsPh$_3$)$_2$, formed in situ, are perfectly suitable.

It can be advantageously prepared in situ by the addition of 2x moles of triphenylarsine to x moles of a zerovalent metal complex such as bis(cyclooctadiene)nickel or (1,5,9-cyclododecatriene)nickel.

When the organic ligand(s) contains (contain) neither phosphorus nor arsenic, it (or they) can be a cyclic hydrocarbon such as cyclooctadiene or cyclododecatriene, to give an example without implying any limitations. Zero-valent nickel complexes such as bis(cyclooctadiene)nickel, and (1,5,9-cyclododecatriene)-nickel are perfectly suitable for implementing the invention.

The complexes according to the invention are generally employed in concentrations of between $10^{-2}$ and $10^{-3}$ mole/litre.

It is important, furthermore, to recall and emphasize that only the complexes in which the nickel is in the zero oxidation state are suitable for implementing the invention.

In the case of the preparation of isocyanates, carbamates and ureas from aromatic halides, the yield is improved by adding small quantities of a Lewis acid to the reaction medium.

On the other hand, in other cases, and especially in the preparation of vinyl, heterocyclic, benzyl or alkyl carbamates, such addition results in a drop in the efficiency of the catalyst system (decrease in yield, very considerable in some cases).

Boron trifluoride etherate, aluminium chloride, zinc chloride, ferric chloride and stannous chloride can be mentioned as examples of Lewis acids which can be used.

They are used in low concentrations, similar to those of the abovementioned nickel complexes. The molar ratio of the Lewis acid to the complex is generally between 0.5 and 2. A ratio which is greater than 2 results in a drop in the yield.

The presence of an organic solvent, in which the organic halide, the catalyst and the Lewis acid (when present) are soluble, and in which the solubility of the metal cyanate used is not zero, is essential.

As a general rule, although nonpolar solvents such as saturated or aromatic hydrocarbons can be suitable whenever the reaction is carried out in the presence of the abovementioned onium halides, a dipolar aprotic solvent, optionally mixed with a hydrocarbon solvent, will be preferable.

As a result of this the solvent will be chosen from ethers, esters, nitriles, sulphoxides or amides with a relatively high boiling point. For example, diglyme, propylene carbonate, N,N-dimethylformamide (DMF), N,N-dimethylacetamide (DMAC), and N-methylpyrrolidone (NMP), optionally mixed with petroleum ether, toluene or xylene, are suitable.

The presence of water has a detrimental effect on the course of the reaction, so that anhydrous solvents must be used to implement the reaction. A particular characteristic of the invention consists in removing the traces of water before the addition of the catalyst, by azeotropic entrainment of water from the reaction mixture, by means of toluene or xylene.

The temperature of the reaction medium may be between +20° C. and 160° C. The optimum temperature depends especially on the organic halide. It is between 140° C. and 155° C. in the case of aromatic or vinyl halides, as well as for halogenated heterocyclic compounds. It can be much lower in the case of allyl halides.

When the initial halides are volatile, the reaction can be carried out in a Schlenck or Carius tube or in an autoclave, under the autogenous pressure of the substrate, sufficient agitation being provided to ensure good contact between the metal cyanate and the organic solution within the reaction medium.

The reaction is continued for the time required to obtain a satisfactory conversion of the organic halide. This reaction time depends on the nature of the organic halide and can range from 1 to 30 hours.

The following examples, which do not imply any limitations, illustrate the invention.

EXAMPLE 1

Preparation of ethyl phenylcarbamate from bromobenzene

Single addition of ethanol.

The following are added in succession into a 20-ml Schlenk tube equipped with a bar magnet and purged with argon:

0.375 g (5.5 mmol) of dry sodium cyanate, 0.085 g (0.1 mmol) of the complex Ni(Ph$_2$—P—CH$_2$—CH$_2$—P—Ph$_2$)$_2$ prepared according to the method described in Inorg. Synth. 1977, 17, 121, 2.5 ml of DMF redistilled over alumina, 0.679 g (4.3 mmol) of bromobenzene, 270 μl of ethanol (4.6 mmol).

The mixture is stirred and heated for 27 h in an oil bath controlled thermostatically at 155° C., and is then returned to ambient temperature. A 68% conversion of bromobenzene and a 27.5% yield of ethylphenylcarbamate are determined by gas phase chromatography (GPC).

EXAMPLE 2

Preparation of ethylphenylcarbamate from bromobenzene

Double addition of ethanol.

The following are added in succession into a 20-ml Schlenk tube equipped with a bar magnet and purged with argon:

0.344 g (5.3 mmol) of dry Sodium cyanate, 0.079 g (0.093 mmol) of the complex Ni(Ph$_2$P—CH$_2$—CH$_2$—PPh$_2$)

2.4 ml of DMF redistilled over alumina, 0.663 g (4.2 mmol) of bromobenzene,

140 μl of ethanol (2.4 mmol).

The mixture is stirred and heated for 16 hours in an oil bath controlled thermostatically at 155° C. The Schlenk tube is cooled rapidly and then 140 μl (2.4 mmol) of ethanol are added under argon. The mixture is heated and stirred for 11 h at 155° C., and is then returned to ambient temperature.

A bromobenzene conversion of 72% and a 35% yield of ethyl phenylcarbamate are determined by GPC.

EXAMPLE 3

Preparation of ethyl phenylcarbamate from bromobenzene

Isolation of the product.

The following are introduced in succession into a 100-ml Schlenk tube equipped with a bar magnet and purged with argon:

1.96 g (30 mmol) of dry sodium cyanate, a mixture of 0.152 g (0.55 mmol) of bis(1,5-cyclooctadiene)nickel prepared according to the method described in Inorg. Synth. 1974, 15,5 and of 0.222 g (0.55 mmol) of 1,2-bis(diphenylphosphino)ethane, 0.058 g (0.3 mmol) of dry stannous chloride, 16.5 ml of DMAC redistilled over alumina, 3.69 g (23.4 mmol) of bromobenzene, 750 μl (12.8 mmol) of ethanol.

The mixture is stirred and heated for 16 h in an oil bath controlled thermostatically at 155° C. The Schlenk tube is cooled quickly and then 750 μl (12.8 mmol) of ethanol are added under argon. The mixture is stirred and heated for 11 h at 155° C. and is then returned to ambient temperature. The reaction mixture is filtered and then the solvent is distilled off. The residue is taken up with ether (3×10 ml). The ether is evaporated off from the ether phase and then the remaining ethyl phenylcarbamate is distilled. (B.p.: 100° C. at 5 mm Hg).

The yield obtained is 33.5%. The product was identified by its IR and NMR spectra: IR spectrum (in CH$_2$Cl$_2$): characteristic bands at 3460 and 1730 cm$^{-1}$.

$^1$H-NMR spectrum (in CCl$_4$)

δ=1.25 ppm (3H, t, J$_{HH}$=7 Hz)

δ=4.1 ppm (2H, q, J$_{HH}$=7 Hz)

δ=6.8–7.5 ppm (6H, complex bands)

EXAMPLE 4

Preparation of ethyl phenylcarbamate

Improvement contributed by carrying out an azeotropic entrainment.

The following are added in succession to a 250-ml two-necked round flask equipped with a bar magnet and purged with argon:

2.36 g (36.4 mmol) of dry sodium cyanate, 4.45 g (28.2 mmol) of bromobenzene, 0.067 g (0.36 mmol) of stannous chloride,
20 ml of DMAC redistilled over alumina,
60 ml of dry toluene.

The mixture is heated in refluxing toluene and then the latter is distilled off. After the flask has been cooled a mixture of 0.182 g (0.655 mmol) of bis(1,5-cyclooctadiene)nickel and of 0.260 g (0.655 mmol) of 1,2-bis(diphenylphosphino)ethane is added, followed by 0.90 ml (15.5 mmol) of ethanol.

The mixture is stirred and heated for 16 h in an oil bath controlled thermostatically at 155° C. The flask is cooled rapidly and then 0.90 ml (15.5 mmol) of ethanol is added under argon. The mixture is stirred and heated for 11 h at 155° C. and is then returned to ambient temperature. The mixture is then treated as in Example 3. The yield of isolated ethyl phenylcarbamate is 42%.

EXAMPLES 5-32

Preparation of ethyl phenylcarbamate from bromobenzene

Effect of various reaction parameters (nature and concentration of the reactants and catalysts, nature of the solvent, method of addition of ethanol).

Table I lists the data and results of various tests carried out in accordance with the "standard" conditions described in detail in Examples 1, 2 (double addition of ethanol), 3 and 4 (formation of a zero-valent nickel complex in situ and addition of a Lewis acid).

In particular, this Table demonstrates the benefit of a portionwise addition of ethanol and of the presence of a Lewis acid within a relatively limited concentration range. On the latter point, it can be seen that, on the contrary, beyond a certain upper concentration limit, the presence of the Lewis acid produces a considerable drop in yield.

Example 30 was carried out with the use of barium cyanate. Since this compound is not commercially available, it was prepared by reacting isocyanic acid with barium carbonate in ether.

The reaction between bromobenzene, barium cyanate and ethanol was followed by thin layer chromatography (TLC). This technique made it possible to demonstrate the formation of ethyl phenylcarbamate.

EXAMPLE 33 and 34

Preparation of ethyl phenylcarbamate from chlorobenzene

A catalyst solution is prepared by dissolving 0.9 g of Ni(cod)$_2$ and 1.3 g of diphenylphosphinoethane in 100 ml of dimethylacetamide under an argon atmosphere.

23.65 g (364 mmol) of NaOCN, 0.6825 g (3.6 mmol) of SnCl$_2$ and 300 ml of toluene are introduced into a 500-cm$^3$ Schlenk tube.

Half of the toluene is evaporated off by distillation at atmospheric pressure, and then the remaining toluene is distilled off under reduced pressure to produce a dry residue.

0.9 g of Ni(cod)$_2$, 1.3 g of diphenylphosphinoethane, 28.7 ml (282 mmol) of chlorobenzene, 9 ml (155. mmol) of ethanol and 100 ml of the catalyst solution prepared above are then added, still under an argon atmosphere.

The quantity of catalyst added in this manner is 1.8 g (6.55 mmol) of Ni(cod)$_2$ with 2.6 g of diphenylphosphinoethane.

The Schlenk tube is kept at 155° C. for 16 hours. After cooling, 9 ml (155 mmol) of ethanol are added and the materials are reheated for 10 hours at 155° C.

After cooling, dimethylacetamide is evaporated off and the residue is taken up with 150 ml of ether. After filtration and evaporation of the ether ethyl phenylcarbamate is distilled under reduced pressure.

The product isolated has a purity of 92% as ethyl phenylcarbamate. The reaction yield is 37.5%.

A test which is similar to the above test is carried out, with the difference that the quantity of added catalyst is 0.3174 g of Ni(Cod)$_2$. 13.5 g of 90% pure ethyl phenylcarbamate are isolated. The yield obtained is 26%, as pure carbamate.

EXAMPLE 35 and 36

Preparation of N-phenyl-N',N'-dibutylurea from bromobenzene and dibutylamine.

Example 35:

The following are added in succession into a 20-ml Schlenk tube equipped with a bar magnet and purged with argon:

0.36 g (5.5 mmol) of dry sodium cyanate, a mixture of 0.028 g (0.1 mmol) of bis(1,5-cyclooctadiene)nickel and of 0.04 g (0.1 mmol) of bis(diphenylphosphino)ethane, 0.100 g (0.055 mmol) of dry stannous chloride, 3 ml of DMAC redistilled over alumina, 0.68 g (4.3 mmol) of bromobenzene, 0.60 g (4.7 mmol) of dibutylamine.

The mixture is stirred and heated for 27 h in an oil bath controlled thermostatically at 155° C. The reaction mixture is cooled to ambient temperature.

The reaction mixture is filtered. The solvent, and then N-phenyl-N',N'-dibutylurea are distilled (120° C. at 0.1 mm Hg). The bromobenzene conversion is 50%. The yield of N-phenyl-N',N'-dibutylurea isolated in this manner is 35%.

The N-phenyl-N',N'-dibutylurea obtained, identified by its NMR and IR spectra, has a melting point of 82° C.

IR spectrum (in CH$_2$Cl$_2$): characteristic bands at 3490 cm$^{-1}$ and 1690 cm$^{-1}$.

$^1$H-NMR spectrum (in CDCl$_3$):
$\delta = 6.97$–$7.53$ ppm (6H, m)
$\delta = 3.07$–$3.7$ ppm (4H, m)
$\delta = 0.72$–$1.72$ ppm (14H, m)

Example 36:

Same operating procedure as in Example 33 but without the presence of stannous chloride.

N-phenyl-N',N'-dibutylurea is isolated in a yield of 28.5%.

Example 37

Preparation of N-styryl-N',N'-diethylurea from bromostyrene and diethylamine.

The same general procedure as in Example 34 was followed, under the particular conditions given in Table II.

N-styryl-N',N'-diethylurea is distilled at 95°–100° C. at 0.1 mm Hg. The yield of N-styryl-N',N'-diethylurea isolated in this manner is 48%. The purity, determined by GPC is greater than 93%. The N-styryl-N',N'-diethylurea obtained was identified by its IR and NMR spectra:

IR (in Nujol): characteristic bands at 3340 cm$^{-1}$, 2950 cm$^{-1}$, 1670 cm$^{-1}$ and 1630 cm$^{-1}$.

$^1$H-NMR (in CDCl$_3$): chemical shifts in ppm relative to TMS:

6.75–7.36: multiplet corresponding to the 5 phenyl ring protons 5.07-6.65: AB system, $J_{AB}=14$ Hz (2 ethylenic pro proton + N-H proton)

3.21: quadruplet corresponding to the 4 CH$_2$ protons of the 2 ethyl chains $J_{HH}=7$ Hz 1.18: triplet corresponding to the 6 CH$_3$ protons of the 2 ethyl chains $J_{HH}=7$ Hz.

EXAMPLE 38

Preparation of N-butyl-N',N'-diethylurea from butyl chloride and diethylamine.

The general procedure followed was the same as in Example 33, under the particular conditions given in Table II.

N-butyl-N',N'-diethylurea is distilled at 60° C. at 0.1 mm Hg. The yield of N-butyl-N',N'-diethylurea isolated in this manner is 35%. N-butyl-N',N'-diethylurea was identified by GPC (comparison with authentic product) and by its IR spectrum (characteristic bands at 3340 cm$^{-1}$ and 1670 cm$^{-1}$).

EXAMPLES 39 to 64

Preparation of various ethyl arylcarbamates from aromatic halides.

Table III lists the tests using simple or condensed, mono- or polysubstituted aromatic mono- or polyhalides, optionally in the presence of an onium salt.

In the case of dihalides, the yields shown are those of a monocarbamate. In the case of dihalide bromides in which the other halogen atom is other than bromine, the yields shown are those for the monocarbamate produced by bromine substitution.

The results show the general character of the reaction and the need to use a catalyst according to the invention in order to see an appreciable yield.

EXAMPLES 65-73

Preparation of ethyl 2-phenylvinylcarbamate from 1-bromo-2-phenylethylene (mixture of the cis and trans isomers).

The general procedure is that described in Examples 1 to 3.

The particular experimental conditions in each test are detailed in Table IV, together with the results obtained. These results show the particularly detrimental effects of the presence of a Lewis acid on the reaction yield, even though the former is used at the same concentration as that which enables an increase in this same yield to be obtained in the case of aromatic halides.

EXAMPLE 74

Preparation of ethyl 2-phenylvinylcarbamate from 1-bromo-2-phenylethylene.

Isolation of the reaction product.

The following are introduced in succession into a 20-ml Schlenk tube equipped with a bar magnet and purged with argon:

0.278 g (4.28 mmol) of dry sodium cyanate, 0.021 g (0.025 mmol) of the complex Ni(Ph$_2$P-CH$_2$-CH$_2$-PPh$_2$)$_2$, 2.65 ml of DMF redistilled over alumina, 0.656 g (3.6 mmol) of 1-bromo-2-phenylethylene, 210 µl (4.6 mmol) of ethanol.

The mixture is stirred and heated for 26 h in an oil bath controlled thermostatically at 143° C. The mixture is then cooled to ambient temperature and then the solvent is distilled under reduced pressure.

The residue is purified on a column of basic alumina (20×2 cm, 50 g A$_2$O$_3$). Elution with mixtures of toluene and ethylacetate gives 0.502 g (2.6 mmol) of ethyl trans-2phenylvinylcarbamate, i.e. a yield of 73%. The product was identified by IR and NMR spectrometry:

IR spectrum (in Nujol): characteristic bands at 3340, 1700 and 1660 cm$_1$ - $^1$H-NMR spectrum (in CDCl$_3$):

$\delta = 1.3$ ppm (3H, t, $J_{HH}=7$ Hz)
$\delta = 4.3$ ppm (2H, q, $J_{HH}=7$ Hz)
$\delta = 6.0$ ppm (2H, AB, $J_{AB}=14$ Hz)
$\delta = 7.3$ ppm (6H, complex bands)

EXAMPLES 75 to 82

Preparation of various ethylvinylcarbamates from vinyl halides.

Table V correlates the tests with the use of various simple or substituted vinyl halides.

The results show the general character of the reaction.

Test 82 was carried out in a stainless steel autoclave equipped with a glass liner and a bar magnet, under the autogenous pressure of the vinyl derivative, at the indicated temperature.

EXAMPLES 83 to 88

Preparation of ethyl carbamates from halogenated heterocyclic compounds.

Table VI correlates the operating conditions and results of tests using various halogenated heterocyclic compounds.

The presence of a Lewis acid results in a reduction in yield.

EXAMPLES 89 to 98

Preparation of ethyl allylcarbamates, ethyl benzylcarbamates and ethyl alkylcarbamates.

Table VII correlates the operating conditions and results of tests with the use of various allyl, benzyl or aliphatic halides.

The results show the improvement brought about by the use of a catalyst according to the invention and the inadvisability of carrying out the reaction in the presence of a Lewis acid (yield reduction).

EXAMPLES 99 and 100

Preparation of phenylisocyanate from sodium cyanate and bromobenzene.

Example 99:

The following are introduced in succession into a 100-ml Schlenk tube equipped with a bar magnet and purged with argon:

1.44 g (22.2 mmol) of dry sodium cyanate, a mixture of 0.111 g (0.4 mmol) of bis(1,5-cyclooctadiene)nickel and 0.16 g (0.4 mmol) of 1,2-bis(diphenylphosphino)ethane (i.e. 0.4 mmol of the complex Ni(dppe)), 0.042 g (0.22 mmol) of dry stannous chloride, 10 ml of NMP redistilled over alumina, 2.71 g (17.2 mmol) of bromobenzene.

The mixture is stirred and heated for 27 h in an oil bath controlled thermostatically at 155° C.

After cooling, the mixture is filtered. 35 ml of ether are added to the filtrate and then the ether phase is recovered. The ether phase is filtered and then ether is evaporated off. The product obtained is distilled and the forerun which contains unreacted starting bromobenzene (boiling point 156° C.), the phenylisocyanate formed (boiling point 162° C.) and traces of NMP (boiling point 210° C.) are collected. These products are separated by being passed, under argon, through a column of silica preheated for 10 min at 50° C. Elution with mixtures of toluene and ethyl acetate enables phenyl isocyanate to be isolated.

The phenyl isocyanate obtained was identified by its refractive index and its IR and NMR spectra:
$n^{20}_D = 1.5360$ IR spectrum: $\nu NCO = 2250$ cm$^{-1}$ $^1$H-NMR spectrum (in CCl$_4$): multiplet at 6.8–7.5 ppm (relative to TMS), corresponding to the 5 aromatic protons.

Example 100:

Same procedure as for Example 99, but without the presence of stannous chloride.

The phenyl isocyanate obtained was isolated and identified in the same manner as in Example 99.

EXAMPLE 101

Preparation of 4-bromophenyl isocyanate from Sodium cyanate and 1,4-dibromobenzene.

The procedure followed was the same as in Example 99 above, but using DMF instead of NMP as solvent.

The 4-bromophenyl isocyanate isolated was identified by its melting point and its IR and NMR spectra:

melting point: 41° C.

IR spectrum (in CH$_2$Cl$_2$): $\nu NCO = 2240$ cm$^{-1}$ $^1$H-NMR spectrum (in CCl$_4$): multiplet at 7.25–7.45 ppm (relative to TMS), corresponding to the 4 aromatic protons.

EXAMPLE 102

Preparation of 4-methoxyphenyl isocyanate from sodium cyanate and 4-bromoanisole.

The procedure followed was the same as in Example 101.

The 4-methoxyphenyl isocyanate isolated was identified by its refractive index and its IR and NMR spectra:
$n^{20}_D = 1.5462$ IR spectrum: $\nu NCO = 2255$ cm$^{-1}$ $^1$H-NMR spectrum (in CCl$_4$): multiplet at 7.25–7.45 ppm (relative to TMS), corresponding to the 4 aromatic protons —singulet at 3.7 ppm (relative to TMS), corresponding to the 3 protons in the methoxy group.

EXAMPLE 103

Preparation of butyl isocyanate from butyl chloride and sodium cyanate.

The following are added in succession into a Schlenk tube equipped with a bar magnet and purged with argon:

2.26 g (34.7 mmol) of dry sodium cyanate, a mixture of 0.075 g (0.269 mmol) of 1,2bis(1,5-cyclooctadiene)nickel and of 0.107 g (0.269 mmol) of 1,2-bis(diphenylphosphino)ethane (i.e. 0.269 mmol of the complex Ni(dppe)), 15 ml of DMF redistilled over alumina, 2.49 g (26.9 mmol) of butyl chloride.

The mixture is stirred and heated for 24 h in an oil bath controlled thermostatically at 140° C.

After cooling, the mixture is filtered and then the filtrate is distilled at atmospheric pressure, to give, first, unreacted butyl chloride (76° C.), and then butyl isocyanate (115° C. The butyl isocyanate isolated in this manner was identified by IR spectrometry and by GPC (comparison with an authentic sample).

EXAMPLE 104

Preparation of butyl isocyanate from butyl chloride and sodium cyanate.

The following are introduced in succession into a 100-cm$^3$ Keller reactor equipped with a top condenser and maintained under a stream of argon:

9.25 g (0.1 mol) of butyl chloride, 8.45 g (0.13 mol) of dry sodium cyanate, 92.5 mg of Ni(dppe)$_2$ (1% by weight relative to butyl chloride), 133.3 mg of dppe 1,2-(diphenylphosphino)ethane, 50 ml of DMAC.

The mixture is heated, with stirring, for 4.5 h at 150° C. After cooling, the mixture is distilled under reduced pressure to separate the mixture of butyl chloride, butyl isocyanate and DMAC from the catalyst.

A fractional distillation of the mixture at atmospheric pressure enabled butyl isocyanate to be recovered, which was analysed and characterized by IR and GPC. The butyl isocyanate yield obtained is 22%.

TABLE I

Preparation of ethyl phenylcarbamate from bromobenzene

| EX No. | Temp. °C. | Time h | NCOM (mmol) | PhBr (mmol) | Solvent (ml) | Catalyst (mmol) | Lewis acid (mmol) | EtOH (mmol) | Conv. % | Yld. % | Remarks |
|---|---|---|---|---|---|---|---|---|---|---|---|
| 1 | 155 | 27 | NCONa 5,5 | 4,3 | DMF 2,5 | Ni(dppe)$_2$ 0,1 | — | 4,6 | 68 | 27,5 | |
| 2 | 155 | 27 | NCONa 5,3 | 4,2 | DMF 2,4 | Ni(dppe)$_2$ 0,093 | — | 4,8 | 72 | 35 | 2 × 2, 4 mmol EtOH at 0 & 16 h |
| 5 | 155 | 27 | NCONa 8,1 | 4,1 | DMF 3,7 | Ni(dppe)$_2$ 0,098 | — | 4,4 | 27 | 7 | |
| 6 | 155 | 27 | NCONa 5,5 | 4,2 | DMAC 3,2 | Ni(dppe)$_2$ 0,1 | — | 4,5 | 93 | 26,5 | |
| 7 | 155 | 27 | NCONa 5,4 | 4,2 | DMAC 3,0 | Ni(dppe)$_2$ 0,1 | — | 4,4 | 83 | 36 | 2 × 2, 2 mmol EtOH at 0 & 16 h |
| 8 | 155 | 27 | NCONa 5,5 | 4,2 | DMAC 3,0 | Ni(dppe)$_2$ 0,1 | SnCl$_2$ 0,033 | 4,5 | 93 | 38 | 2 × 2, 25 mmol EtOH at 0 & 16 h |
| 9 | 155 | 27 | NCONa 5,5 | 4,3 | DMAC 3,0 | Ni(dppe)$_2$ 0,1 | SnCl$_2$ 0,055 | 4,8 | 91 | 46 | 2 × 2, 4 mmol EtOH at 0 & 16 h |
| 10 | 155 | 27 | NCONa 5,4 | 4,2 | DMAC 3,0 | Ni(dppe)$_2$ 0,1 | SnCl$_2$ 0,1 | 4,5 | 70 | 30 | 2 × 2, 25 mmol EtOH at 0 & 16 h |
| 11 | 155 | 27 | NCONa 5,5 | 4,2 | DMAC 3,0 | Ni(dppe)$_2$ 0,1 | SnCl$_2$ 0,5 | 4,6 | 80 | 13 | 2 × 2, 23 mmol EtOH at 0 & 16 h |
| 12 | 155 | 27 | NCONa 5,5 | 4,2 | DMAC 3,0 | Ni(dppe)$_2$ 0,1 | SnCl$_2$ 1,0 | 4,6 | 78 | 7 | 2 × 2, 3 mmol EtOH at 0 & 16 h |
| 13 | 155 | 27 | NCONa 5,4 | 4,3 | DMAC | Ni(dppe) 0,1 | — | 4,6 | 50 | 32 | |

TABLE I-continued

Preparation of ethyl phenylcarbamate from bromobenzene

| EX No. | Temp. °C. | Time h | NCOM (mmol) | PhBr (mmol) | Solvent (ml) | Catalyst (mmol) | Lewis acid (mmol) | EtOH (mmol) | Conv. % | Yld. % | Remarks |
|---|---|---|---|---|---|---|---|---|---|---|---|
| 14 | 155 | 27 | NCONa 5,5 | 4,2 | DMAC 3,0 | Ni(dppe) 0,1 | SnCl$_2$ 0,055 | 4,5 | 90 | 42 | |
| 15 | 155 | 27 | NCONa 5,5 | 4,2 | DMAC 3,0 | Ni(dppe) 0,1 | SnCl$_2$ 0,1 | 4,5 | 65 | 35,5 | |
| 16 | 155 | 27 | NCONa 5,5 | 4,2 | DMAC 3,0 | Ni(dppe) 0,1 | SnCl$_2$ 0,055 | 4,6 | 90 | 48 | 2 × 2, 3 mmol EtOH at 0 & 16 h |
| 17 | 155 | 27 | NCONa 5,5 | 4,3 | DMAC 3,0 | Ni(dppm)$_2$ 0,1 | SnCl$_2$ 0,055 | 4,6 | 83 | 23 | 2 × 2, 3 mmol EtOH at 0 & 16 h |
| 18 | 155 | 27 | NCONa 5,5 | 4,3 | DMAC 3,0 | Ni(dppb)$_2$ 0,1 | SnCl$_2$ 0,055 | 4,6 | 90 | 25[a] | 2 × 2, 3 mmol EtOH at 0 & 16 h |
| 19 | 155 | 27 | NCONa 5,5 | 4,3 | DMAC 3,0 | Ni(dppm) 0,1 | SnCl$_2$ 0,055 | 4,6 | 95 | 35 | 2 × 2, 3 mmol EtOH at 0 & 16 h |
| 20 | 155 | 27 | NCONa 5,5 | 4,3 | DMAC 3,0 | Ni(dppp) 0,1 | SnCl$_2$ 0,055 | 4,6 | 85 | 37[a] | 2 × 2, 3 mmol EtOH at 0 & 16 h |
| 21 | 155 | 27 | NCONa 5,5 | 4,3 | DMAC 3,0 | Ni(dppb) 0,1 | SnCl$_2$ 0,055 | 4,6 | 90 | 41[a] | 2 × 2, 3 mmol EtOH at 0 & 16 h |
| 22 | 155 | 27 | NCONa 5,5 | 4,3 | DMAC 3,0 | Ni(PBu$_3$)$_2$ 0,1 | SnCl$_2$ 0,055 | 4,5 | 90 | 30 | 2 × 2, 25 mmol EtOH at 0 & 16 h |
| 23 | 155 | 27 | NCONa 5,5 | 4,3 | DMAC 3,0 | Ni(PCy$_3$)$_2$ 0,1 | SnCl$_2$ 0,055 | 4,5 | 95 | 32 | 2 × 2, 25 mmol EtOH at 0 & 16 h |
| 24 | 155 | 27 | NCONa 5,4 | 4,3 | DMF 3,0 | Ni(dppe) 0,1 | ZnCl$_2$ 0,055 | 4,6 | 70 | 32 | |
| 25 | 155 | 27 | NCONa 5,4 | 4,3 | DMF 3,0 | Ni(dppe) 0,1 | ZnCl$_2$ 0,055 | 4,6 | 75 | 32 | |
| 26 | 155 | 27 | NCONa 5,4 | 4,3 | DMAC 3,0 | Ni(dppe) 0,1 | ZnCl$_2$ 0,055 | 4,6 | 75 | 32 | |
| 27 | 155 | 27 | NCONa 5,4 | 4,3 | DMAC 3,0 | Ni(dppe) 0,1 | ZnCl$_2$ 0,055 | 4,6 | 80 | 37 | |
| 28 | 155 | 27 | NCONa 5,5 | 4,3 | DMAC 3,0 | Ni(AsPh$_3$)$_2$ 0,1 | SnCl$_2$ 0,055 | 4,7 | 75 | 45[a] | 2 × 2, 25 mmol EtOH at 0 & 16 h |
| 29 | 155 | 27 | NCONa 5,5 | 4,3 | DMAC 3,0 | Ni(cod)$_2$ 0,1 | SnCl$_2$ 0,055 | 4,7 | 90 | 28[a] | 2 × 2, 35 mmol EtOH at 0 & 16 h |
| 30 | 155 | 27 | (NOC$_2$) Ba$_3$ | 4,3 | DMAC 3,0 | Ni(dppe)$_2$ 0,1 | SnCl$_2$ 0,055 | 4,7 | ND | ND | Formation of ethyl phenyl-carbamate |
| 31 | 150 | 16 | NCOK 6 | 4,5 | DMF 2,0 | Ni(dppe)(PPh$_3$) 0,3 | — | 5,0 | 40 | 10 | Formation of diphenyl |
| 32 | 100 | 16 | NCOK 6 | 4,5 | DMF 2,0 | Ni(PBu$_3$)$_2$ 0,1 | — | 5,0 | 10 | 2 | Formation of diphenyl | dppm = bis(diphenylphosphino)methane
dppp = bis(diphenylphosphino)propane
ND = not determined
[a]Yield of isolated product

TABLE II

Preparation of N—styryl-N',N'—diethylurea and of N—butyl-N',N'—diethylurea
Experimental conditions

| Example | Temp. °C. | Time h | NCOM mmol | Halogenated derivative mmol | Solvent ml | Catalyst mmol | Lewis acid mmol | Et$_2$NH mmol | Conv. % | Yld. % |
|---|---|---|---|---|---|---|---|---|---|---|
| 37 | 143 | 26 | NCONa 17,2 | Ph—CH=CH—Br 14,3 | D.M.F. 10 | Ni(dppe)$_2$ 0,1 | — | 19 | 90 | 48 |
| 38 | 140 | 24 | NCONa 12,9 | C$_4$H$_9$Cl 10 | D.M.F. 6 | Ni(dppe)$_2$ 0,1 | SnCl$_2$ 0,1 | 11 | 85 | 35 |

TABLE III

Preparation of various ethyl arylcarbamates from aromatic halides

| EX No. | Temp. °C. | Time h | NCOM (mmol) | Aromatic halide (mmol) | Solvent (ml) | Catalyst (mmol) | Lewis acid (mmol) | EtOH (mmol) | Conv. % | Yld. % | Remarks |
|---|---|---|---|---|---|---|---|---|---|---|---|
| 33 | 155 | 26 | NCONa 364 | C$_6$H$_5$Cl 282 | DMAC | Ni(dppe) 6,55 | SnCl$_2$ 3,6 | 310 | 90 | 37,5[b] | |
| 34 | 155 | 26 | NCONa 364 | C$_6$H$_5$Cl 282 (bromo-4- | DMAC | Ni(dppe) 1,15 | SnCl$_2$ 3,6 | 310 | 82 | 26[b] | |
| 39 | 155 | 27 | NCONa 5,4 | p.BRC$_9$H$_{11}$ cumene) | DMAC 3 | Ni(dppe) 0,1 | SnCl$_2$ 0,055 | 4,6 | 90 | 45[b] | |
| 40 | 155 | 27 | NCONa 5,4 | C$_6$H$_5$Cl 4,2 | DMAC 3 | Ni(dppe) 0,1 | SnCl$_2$ 0,055 | 4,6 | 70 | 25[a] | |
| 41 | 155 | 27 | NCONa 5,4 | C$_6$H$_5$Cl 4,2 | DMAC 3 | — | — | 4,6 | <1 | | Blank test |
| 42 | 155 | 27 | NCONa 5,4 | C$_6$H$_5$Cl 4,2 | DMAC 3 | Ni(dppe) 0,1 | SnCl$_2$ 0,055 | 4,6 | >85 | 45[b] | 10% mol |Bu$_4$N|Br |
| 43 | 155 | 27 | NCONa 5,4 | C$_6$H$_5$Cl 4,2 | DMAC 3 | Ni(dppe) 0,1 | SnCl$_2$ | 4,6 | 85 | 27[b] | 5% mol |

TABLE III-continued

Preparation of various ethyl arylcarbamates from aromatic halides

| EX No. | Temp. °C. | Time h | NCOM (mmol) | Aromatic halide (mmol) | Solvent (ml) | Catalyst (mmol) | Lewis acid (mmol) | EtOH (mmol) | Conv. % | Yld. % | Remarks |
|---|---|---|---|---|---|---|---|---|---|---|---|
| 44 | 155 | 27 | NCONa 5,4 | $C_6H_5Cl$ 4,2 | DMAC 3 | Ni(dppe) 0,1 | $SnCl_2$ 0,055 | 4,6 | 88 | 17[b] | |Bu_4N|Br 1% mol |
| 45 | 155 | 27 | NCONa 5,4 | $C_6H_5Cl$ 4,2 | DMAC 3 | Ni(dppe) 0,1 | $SnCl_2$ 0,055 | 4,6 | 60 | 20[b] | |Bu_4N|Br 20% mol KBr |
| 46 | 155 | 27 | NCONa 5,4 | $p\text{-MeOC}_6H_4Cl$ 4,2 | DMAC 3 | Ni(dppe) 0,1 | SnCl 0,055 | 4,6 | 50 | 14[b] | |
| 47 | 155 | 27 | NCONa 5,4 | $p\text{-MeOC}_6H_4Cl$ 4,2 | DMAC 3 | Ni(dppe) 0,1 | $SnCl_2$ 0,055 | 4,6 | 65 | 32[b] | 10% mol |Bu_4N|Br |
| 48 | 155 | 27 | NCONa 5,4 | $p\text{-MeOC}_6H_4Br$ 4,2 | DMAC 3 | Ni(dppe) 0,1 | $SnCl_2$ 0,055 | 4,6 | 60 | 47[b] | |
| 49 | 155 | 27 | NCONa 5,4 | $p\text{-MeOC}_6H_4Br$ 4,2 | DMAC 3 | — | — | 4,6 | <1 | 0 | Blank test |
| 50 | 155 | 27 | NCONa 5,4 | $p\text{-MeC}_6H_4Br$ 4,2 | DMAC 3 | Ni(dppe) 0,1 | $SnCl_2$ 0,055 | 4,6 | 80 | 33[b] | |
| 51 | 155 | 27 | NCONa 5,4 | $m\text{-MeC}_6H_4Br$ 4,2 | DMAC 3 | Ni(dppe) 0,1 | $SnCl_2$ 0,055 | 4,6 | 80 | 20[b] | |
| 52 | 155 | 27 | NCONa 5,4 | $p\text{-ClC}_6H_4Br$ 4,2 | DMAC 3 | Ni(dppe) 0,1 | $SnCl_2$ 0,055 | 4,6 | >80 | 27[b] | monocarbamate |
| 53 | 155 | 27 | NCONa 5,4 | $o\text{-ClC}_6H_4Br$ 4,2 | DMAC 3 | Ni(dppe) 0,1 | $SnCl_2$ 0,055 | 4,6 | 50 | 10[a] | monocarbamate |
| 54 | 155 | 27 | NCONa 5,4 | $p\text{-FC}_6H_4Br$ 4,2 | DMAC 3 | Ni(dppe) 0,1 | $SnCl_2$ 0,055 | 4,6 | 70 | 18[b] | monocarbamate |
| 55 | 155 | 27 | NCONa 5,4 | $O_2N\text{—}C_6H_4Br$ 4,2 | DMAC 3 | Ni(dppe) 0,1 | $SnCl_2$ 0,055 | 4,6 | 50 | 20[a] | |
| 56 | 155 | 27 | NCONa 5,4 | $F_3C\text{—}C_6H_4Br$ | DMAC 3 | Ni(dppe) 0,1 | $SnCl_2$ 0,055 | 4,6 | 85 | 57[b] | |
| 57 | 155 | 27 | NCONa 5,4 | $p\text{-}C_6H_4Br_2$ 4,2 | DMAC 3 | Ni(dppe) 0,1 | $SnCl_2$ 0,055 | 4,6 | 70 | 32[b] | monocarbamate |
| 58 | 155 | 27 | NCONa 5,4 | $p\text{-}C_2H_3\text{—}C_6H_4Br$ 4,2 | DMAC 3 | Ni(dppe) 0,1 | $SnCl_2$ 0,055 | 4,6 | — | 8[b] | |
| 59 | 155 | 27 | NCONa 5,4 | $4,4'C_{12}H_8Br_2$ 4,2 | DMAC 3 | Ni(dppe) 0,1 | $SnCl_2$ 0,055 | 4,6 | 50 | 25[b] | monocarbamate |
| 60 | 155 | 27 | NCONa 5,4 | $m\text{-}C_6H_4Br_2$ 4,2 | DMAC 3 | Ni(dppe) 0,1 | $SnCl_2$ 0,055 | 4,6 | 50 | 22[b] | monocarbamate |
| 61 | 155 | 27 | NCONa 5,4 | $\alpha\text{-ClC}_{10}H_7$ 4,2 | DMAC 3 | Ni(dppe) 0,1 | $SnCl_2$ 0,055 | 4,6 | 50 | 40[b] | |
| 62 | 155 | 27 | NCONa 5,4 | $\alpha\text{-ClC}_{10}H_7$ 4,2 | DMAC 3 | Ni(dppe) 0,1 | $SnCl_2$ 0,055 | 4,6 | 75 | 53[b] | 10 mol % |Bu_4N|Br |
| 63 | 155 | 27 | NCONa 5,4 | $\alpha\text{-BrC}_{10}H_7$ 4,2 | DMAC 3 | Ni(dppe) 0,1 | $SnCl_2$ 0,055 | 4,6 | 90 | 52[b] | |
| 64 | 155 | 27 | NCONa 5,4 | $\beta\text{-BrC}_{10}H_7$ 4,2 | DMAC 3 | Ni(dppe) 0,1 | $SnCl_2$ 0,055 | 4,6 | 100 | 33[b] | |

[a]Determined by GPC
[b]Isolated

TABLE IV

Preparation of ethyl 2-phenylvinylcarbamate from 1-bromo-2-phenylethylene

| EX No. | Temp. °C. | Time h | NCOM (mmol) | PhCH=CHBr (mmol) | Solvent (ml) | Catalyst (mmol) | Lewis acid (mmol) | EtOH (mmol) | Conv. % | Yield % (trans:cis) | Remarks |
|---|---|---|---|---|---|---|---|---|---|---|---|
| 65 | 143 | 26 | NCONa 17,2 | 14,5 | DMF 10 | Ni(dppe)$_2$ 0,1 | — | 19 | 99 | 90 (91:9) | |
| 66 | 143 | 26 | NCONa 17,1 | 14,5 | DMF 10 | Ni(dppe)$_2$ 0,1 | $SnCl_2$ 0,055 | 19 | 85 | 16 (89:11) | |
| 67 | 143 | 26 | NCONa 17,2 | 14,4 | DMF 10 | Ni(dppe)$_2$ 0,1 | — | 19 | 100 | 76 (82:18) | 2 × 9, 5 mmol EtOH 0 & 16 h |
| 68 | 143 | 26 | NCONa 17,2 | 14,5 | DMF 10 | Ni(dppe)$_2$ 0,1 | — | 19 | 100 | 90 (91:9) | |
| 69 | 143 | 26 | NCONa 17,2 | 14,5 | DMAC 13,3 | Ni(dppe)$_2$ 0,1 | $SnCl_2$ 0,055 | 19 | 100 | 17,5 (85:15) | |
| 70 | 143 | 26 | NCONa 17,2 | 14,5 | DMAC 13,3 | Ni(dppe)$_2$ 0,1 | — | 19 | 100 | 72 (88:12) | 2 × 9, 5 mmol EtOH 0 & 16 h |
| 71 | 143 | 26 | NCONa 17,2 | 14,5 | DMAC 13,3 | Ni(dppe) 0,1 | — | 19 | 90 | 35 (90:10) | |
| 72 | 155 | 27 | NCONa 16,9 | 14,3 | DMF 10 | Ni(PBu$_3$)$_4$ 0,1 | $SnCl_2$ 0,055 | 18,4 | 80 | 45 (88:12) | complex formed in situ |
| 73 | 140 | 27 | NCONa 16,9 | 14,3 | DMF 10 | |CuI(PBu$_3$)|$_4$ | — | 15,7 | 80 | 0 | |

TABLE V

Preparation of various ethyl vinylcarbamates from vinyl halides

| EX. No. | Temp. °C. | Time h | NCOM (mmol) | Vinyl halide (mmol) | Solvent (ml) | Catalyst (mmol) | EtOH (mmol) | Conv. % | Yld. % | Remarks |
|---|---|---|---|---|---|---|---|---|---|---|
| 75 | 143 | 26 | NCONa 17,2 | PhCH=CHCl 14,5 | DMF 10 | Ni(dppe)$_2$ 0,1 | 19 | 50 | 15 | |
| 76 | 143 | 26 | NCONa 17,2 | PhCH=CHCl 14,5 | DMF 10 | Ni(dppe)$_2$ 0,1 | 19 | 80 | 35 | 10 mol % \|Bu$_4$N\|Br complex formed in situ; +SnCl$_2$ |
| 77 | 155 | 27 | NCONa 16,9 | PhCH=CHCl 14,3 | DMF 10 | Ni(PBu$_3$)$_4$ 0,1 | 18,4 | 80 | 45 | 0.055 mmol |
| 78 | 140 | 26 | NCONa 16,9 | PhCH=CHCl 14,3 | DMF 10 | \|CuI(PBu$_3$)\| 0,1 | 15,7 | 80 | 0 | |
| 79 | 143 | 26 | NCONa 17,2 | 3,4(MeO)$_2$C$_6$H$_3$—C$_2$H$_2$Br 14,5 | DMF 10 | Ni(dppe)$_2$ 0,1 | 19 | 100 | 50 | |
| 80 | 143 | 26 | NCONa 17,2 | EtOCH=CHBr 14,5 | DMF 10 | Ni(dppe)$_2$ 0,1 | 19 | 70 | 11 | In Schlenk tube |
| 81 | 143 | 26 | NCONa 17,2 | MeCH=CHBr 14,5 | DMF 10 | Ni(dppe)$_2$ 0,1 | 19 | 85 | 26 | In Schlenk tube |
| 82 | 143 | 26 | NCONa 17,2 | CH$_2$=CHBr 14,5 | DMF 10 | Ni(dppe)$_2$ 0,1 | 19 | — | 15 | In autoclave |

TABLE VI

Preparation of ethyl carbamates from halogenated heterocyclic compounds

| EX. No. | Temp. °C. | Time h | NCOM (mmol) | Heterocyclic halide (mmol) | Solvent (ml) | Catalyst (mmol) | EtOH (mmol) | Conv. % | Yld. % | Remarks |
|---|---|---|---|---|---|---|---|---|---|---|
| 83 | 140 | 27 | NCONa 5,5 | 2-BrC$_5$H$_4$N 4,3 | DMAC 3 | Ni(dppe) 0,1 | 4,7 | 35 | 15 | — |
| 84 | 140 | 27 | NCONa 5,5 | 2-BrC$_5$H$_4$N 4,3 | DMAC 3 | Ni(dppe) 0,1 | 4,7 | 25 | 7 | SnCl$_2$ 0,055 mmol |
| 85 | 140 | 27 | NCONa 5,4 | 3-BrC$_5$H$_4$N 4,3 | DMAC 3 | Ni(dppe) 0,1 | 4,6 | 60 | 31 | SnCl$_2$ 0,055 mmol |
| 86 | 140 | 27 | NCONa 5,5 | 4-BrC$_5$H$_4$NH$^+$Cl— 4,3 | DMAC 3 | Ni(dppe) 0,1 | 4,7 | — | ≅4 | SnCl$_2$ 0,055 mmol |
| 87 | 140 | 27 | NCONa 5,4 | 4-BrC$_9$H$_7$N 4,3 | DMAC 3 | Ni(dppe) 0,1 | 4,7 | 70 | 25 | SnCl$_2$ 0,055 mmol |
| 88 | 140 | 27 | NCONa 5,4 | 3-BrC$_4$H$_3$O 4,3 | DMAC 3 | Ni(dppe) 0,1 | 4,7 | 90 | 10 | SnCl$_2$ 0,055 mmol |

TABLE VII

Preparation of ethyl allyl-, benzyl-and alkylcarbamates from the corresponding organic halides

| EX. No. | Temp. °C. | Time h | NCOM (mmol) | Organic halides (mmol) | Solvent (ml) | Catalyst (mmol) | EtOH (mmol) | Conv. % | Yld. % | Remarks |
|---|---|---|---|---|---|---|---|---|---|---|
| 89 | 140 | 24 | NCONa 12, | Me-2 C$_3$H$_4$Cl 10 | DMF 6 | Ni(dppe) 0,1 | 11 | 90 | 41 | SnCl$_2$ 0,1 mmol |
| 90 | 140 | 24 | NCONa 12, | Me-2 C$_3$H$_4$Cl 10 | DMF 6 | — | 11 | 90 | 33 | Blank test |
| 91 | 140 | 24 | NCONa 12, | PhC$_3$H$_4$Br 10 | DMF 6 | Ni(dppe) 0,1 | 11 | 85 | 30 | SnCl$_2$ 0,1 mmol |
| 92 | 140 | 24 | NCONa 12, | PhC$_3$H$_4$Br 10 | DMF 6 | — | 11 | 80 | 20 | Blank test |
| 93 | 155 | 24 | NCONa 12, | PhCH$_2$Cl 10 | DMF 6 | Ni(dppe) 0,1 | 11 | 90 | 73 | — |
| 94 | 155 | 24 | NCONa 12, | PhCH$_2$Cl 10 | DMF 6 | Ni(dppe) | 11 | 90 | 60 | SnCl 0,1 mmol |
| 95 | 140 | 24 | NCONa 12, | PhCH Cl 10 | DMF 6 | — | 11 | 90 | 43 | Blank test |
| 96 | 140 | 24 | NCONa 12, | C$_4$H$_9$Cl 10 | DMF 6 | Ni(dppe) 0,1 | 11 | 95 | 70 | — |
| 97 | 140 | 24 | NCONa 12,9 | C$_4$H$_9$Cl 10 | DMF 6 | Ni(dppe) 0,1 | 11 | 90 | 62 | SnCl$_2$ 0,1 mmol |
| 98 | 140 | 24 | NCONa 12,9 | C$_4$H$_9$Cl 10 | DMF 6 | — | 11 | 90 | 35 | Blank test |

We claim:

1. Process for the synthesis of isocyanates by the reaction of an organic halide chosen from the group consisting of: acyclic or cyclic vinyl halides, optionally substituted by at least one alkyl or aryl group; simple or condensed aromatic halides, optionally substituted by at least one alkyl, vinyl, aryl, halo or alkoxy group; halogenated heterocyclic compounds; allyl halides optionally substituted by at least one alkyl or aryl group; straight-chain or branched or cyclic aliphatic halides; and benzyl halides, optionally substituted by at least one alkyl or aryl group with a metal cyanate in an organic medium containing at least one solvent chosen from the group consisting of di-polar aprotic solvents, saturated hydrocarbons and aromatic hydrocarbons, wherein said reaction takes place in the presence of a catalyst consisting of a complex of nickel with a phosphorus, arsenic or cyclic hydrocarbon organic ligand or mixtures thereof, and, in said complex, nickel is in a zero oxidation state.

2. Process according to claim 1 wherein said organic halide is chosen from the group consisting of:
    acyclic or cyclic vinyl halides, optionally substituted by at least one alkyl or aryl group;
    simple or condensed aromatic halides, optionally substituted by at least one alkyl, vinyl, aryl, halo or alkoxy group.

3. Process according to claim 1 wherein said organic halide is an organic chloride, and wherein an alkali metal or onium bromide or iodide is added to the reaction medium.

4. Process according to claim 3, wherein the molar fraction of said alkali metal or onium bromide or iodide is of the order of 10% relative to said organic chloride.

5. Process according to claim 1 wherein said metal cyanate is sodium cyanate.

6. Process according to claim 1 wherein said ligads are chosen from the group consisting of teritary arsines, basic phosphines and bidentate phosphines.

7. Process according to claim 6, wherein said basic phosphine is chosen from the group consisting of triphenylphosphine, tributylphosphine and tricyclohexylphosphine.

8. Process according to claim 6, wherein said bidentate phosphine is a bis(diphenylphosphino)polymethylene.

9. Process according to claim 8, wherein said bis(diphenylphosphino)polymethylene is bis(diphanylphosphino)ethane or bis(diphenylphosphino)butane.

10. Process according to claim 6, wherein said tertiary arsine is triphenylarsine.

11. Process according to claim 1 wherein said reaction of said organic halide with said metal cyanate in said organic medium also takes place in the presence of a Lewis acid.

12. Process according to claim 1 wherein said organic medium contains a dipolar aprotic solvent.

13. Process according to claim 12, wherein said organic medium also contains a hydrocarbon solvent.

14. Process according to claim 1 wherein azeotropic distillation and removal of water are carried out before the addition of said catalyst.

* * * * *